(12) United States Patent
McFadden

(10) Patent No.: US 6,575,167 B1
(45) Date of Patent: Jun. 10, 2003

(54) PROTECTION DEVICE FOR HAND HELD ULTRASOUND NEEDLE PROCEDURES

(76) Inventor: Jeannie S. McFadden, 2008 S. Warren, Sedalia, MO (US) 65301

( * ) Notice: Subject to any disclaimer, the term of this patent is extended or adjusted under 35 U.S.C. 154(b) by 0 days.

(21) Appl. No.: 09/363,580

(22) Filed: Jul. 29, 1999

(51) Int. Cl.$^7$ .................................................. A61F 5/37
(52) U.S. Cl. ...................... 128/846; 128/878; 128/879; 604/263
(58) Field of Search .............................. 128/845, 846, 128/877, 878, 879; 604/263

(56) References Cited

U.S. PATENT DOCUMENTS

| | | | |
|---|---|---|---|
| 4,071,913 A | 2/1978 | Rector | 2/20 |
| 4,657,282 A | 4/1987 | Koch | 280/821 |
| 4,884,300 A | 12/1989 | Vistin | 2/162 |
| 4,976,254 A | * 12/1990 | Dash | 128/857 |
| 5,007,674 A | * 4/1991 | Franc | 297/184 |
| 5,295,269 A | 3/1994 | Ballard | 2/18 |
| 5,566,390 A | 10/1996 | Clancy | 2/16 |
| 5,581,811 A | 12/1996 | Cohen et al. | 2/161 |
| 5,624,404 A | 4/1997 | Fisler | 604/187 |
| 5,782,750 A | 7/1998 | Gluskin | 600/119 |

* cited by examiner

Primary Examiner—Michael A. Brown
(74) Attorney, Agent, or Firm—Richard J. Grundstrom

(57) ABSTRACT

A protection device for hand held ultrasound needle procedures that can be generally described as a shield attachable to a transducer. The shield protects the hand from needle puncture. The shield can be made from either a flexible or a rigid material which is resistant to needle punctures, by both or either a hand directed needle or a mechanically fired needle. The shield is bent in the shape of an arc. The arc has a first apex at the top of the arc. A second apex is located at the bottom of the arc. A first receiver and a first method of securing an upper end of a transducer, or cable attached thereto, is located at the first apex. A second receiver and a second method of securement is located at the second apex to receive and secure a lower end or head of a transducer to the shield. The device attaches above or over a biopsy guide typically located on the head of a transducer or it attaches directly to the transducer. It allows the technologist to grasp the transducer within the arc of the shield and use the transducer in a normal manner while providing a barrier between the directed biopsy needle and the technologist's or physician's hand. The receiver and method of securement can be as simple as an opening with hook and loop material or as elaborate as specialty latches designed to specifically attach to the transducer.

15 Claims, 5 Drawing Sheets

PROTECTION DEVICE FOR HAND HELD ULTRASOUND NEEDLE PROCEDURES

BACKGROUND OF THE INVENTION

The present invention relates to a protection device for hand held ultrasound transducers during needle guided procedures and relates particularity to a shield that protects the hand of the technologist/physician from accidental needle punctures during ultrasound procedures in which a technologist or physician uses a transducer, scope or other hand held imaging devices with a needle guide for biopsy/aspiration positioning.

The shield or protective device of this invention is typically used with ultrasound transducers having a needle guide attachment. The combination transducer and needle guide are used to properly position the needle for accurate biopsy/aspiration of the lesion in question. The transducer provides the a real-time image of the internal body area in question and can be saved in frozen format for documentation. Once the proper location has been designated by the transducer, a needle, catheter or other body piercing device is inserted into the needle guide on the head of the transducer. The technologist/physician can view the monitor as the needle or catheter is inserted through the guide. This arrangement allows the technologist/physician to specifically and exactly position the needle or catheter with a very high degree of precision. Since the technologist/physician is watching the monitor and not the needle the technologist/physician holding the transducer often inadvertently gets stuck with the contaminated needle, resulting in additional costs of health care professional and patient testing for HIV/AIDS and Hepatitis viruses. Prior to this invention, there is no known shielding device to protect the hand of the health care professional from needle injuries during these types of procedures.

There are many different types of transducers known and used. They can be basically categorized by the shape of the head and it's use. There are linear array, curved array, sector array and endocavity transducers. The linear array transducer has a flat, smooth, and straight area that contacts the skin of the patient. The curved array has, as the name suggests, a curved surface at the head area that contacts the skin. The sector array has a rectangular or square area on the head. Endocavity transducers are designed to be inserted into body orifices such as the rectum, vagina or esophagus. Each have particular uses, and advantages or disadvantages based upon the particular procedure being performed and body part being imaged. The device of this invention can be made specific for a specific type or brand of transducer, or universally adaptable to any of these transducers or any other type that do not fall in these specific categories.

Accordingly, it is an object of the present invention to provide a protection device for hand held ultrasound guided needle procedures adapted to protect the health care professional's hand from inadvertent punctures from contaminated needles. With the protection device, for hand held ultrasound guided needle procedures, of this invention, it has been found that the hand is protected and covered with a shield that eliminates the majority, if not all, of inadvertent needle punctures.

Another object of the present invention is to provide a protection device for hand held ultrasound guided needle procedures that can be universally used on any type of transducer or similar device utilizing needle guidance. The universal application of this invention may be preferred because a single shield design would fit and function with all types of transducers and manufacturers. This would help to lower cost and inventory in locations that have several different types of transducers in use.

A further object of the present invention is to provide a protection device for hand held ultrasound guided needle procedures that can be made for a specific application or device. A shield of this invention can be made to specifically fit a specific type of transducer. This may be desired for exactness of fit, to prevent loose fitting of the shield to a transducer, and to provide a particular manufacturer with a means of providing a shield for a specific device.

To accomplish the foregoing and other objects of this invention there is provided a protection device for hand held ultrasound guided needle procedures and more particularly to a shield that protects the hand of the ultrasound technologist/physician from punctures by contaminated needles during ultrasound guided needle procedures.

SUMMARY OF THE INVENTION

The protection device for hand held ultrasound guided needle procedures of this invention includes a protective device basically being a shield made from a shielding material shaped to cover the hand and having a means to attach and secure the shield to an ultrasound transducer or similar device. The device can be attached above or over a biopsy guide or directly to a transducer. It allows the technologist/physician to grasp the transducer in a normal manner while providing a barrier between the directed biopsy needle and the health professional's hand. The shield material must be resistant to needle puncture, both by hand guided needles and core biopsy needles used with mechanical biopsy guns that thrust the needle into the tissues with a particular force. The material could be disposable or readily cleanable, rigid or flexible depending on the embodiment and desires of the consumer.

The shield is formed in a basic arc that fits around the hand. At the top and bottom apex of the arc, provisions are made for attaching and securing the transducer. The attachment provisions can be as simple as an opening with a hook and loop material or as elaborate as special latches or fittings designed to specifically attach to a specific transducer and/or manufacturers design.

In operation, the shield is attached to the transducer using the attatchment provisions. The technologist/physician can then insert their hand into the arc of the shield to grasp the transducer. The transducer can then be used in the normal fashion. As the physician performs a biopsy, aspiration, stent, catheter placement or any other procedures in which the attached needle guide is used, the technologist's/physician's hand is protected from punctures by contaminated sharp medical devices such as needles.

The above mentioned and other objects, and features of the present invention will be better understood and appreciated from the following detailed description of the main embodiment thereof, selected for purposes of illustration and shown in the accompanying drawings.

DETAILED DESCRIPTION

Figure 1:
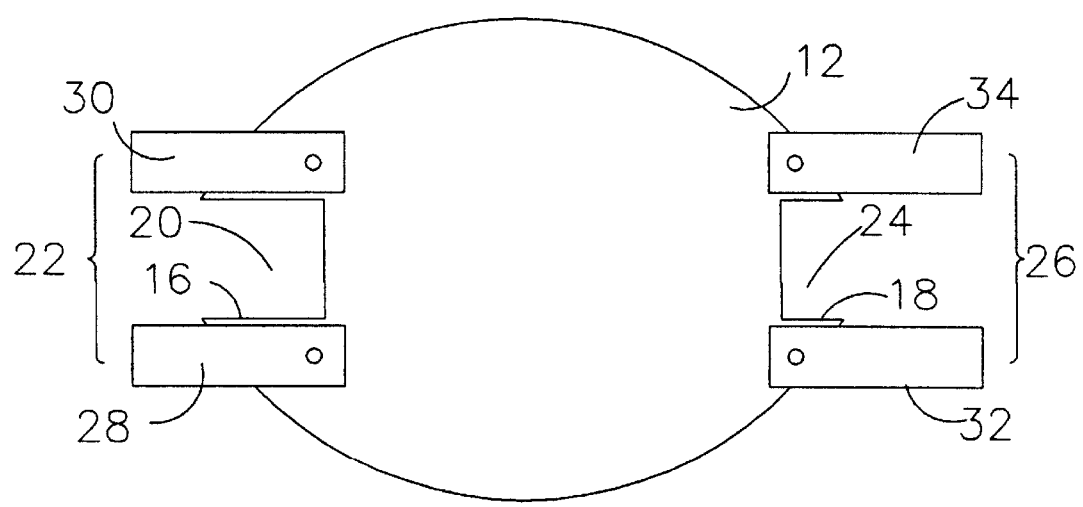
FIG. 1 shows the protective device of this invention with the shield being in a flat configuration, which is a representation of one embodiment of this invention.

Referring now to the drawings there is shown preferred embodiments of the protection device 10 for hand held ultrasound needle procedures of this invention. The protective device 10 being a shield 12 made from a shielding material shaped to cover the hand 6 and having a means to be attached and secured to an ultrasound transducer 8, or similar device. The protective device 10 attaches above or over a biopsy guide 4 or directly to the transducer 8. It allows the technologist/physician to grasp the transducer 8 in a normal manner while providing a barrier between the directed biopsy needle and the technologist's hand 6. The shield material must be resistant to needle puncture but yet be readily cleanable and perhaps autoclavable or preferably disposable. The shield material could be aluminum or other light weight metals, plastic, plexiglass, acrylics, fibrous materials or any other suitable type material. It can also be flexible or rigid depending on the particular configurations and desires. The material ideally, in a preferred embodiment, would be disposable for added sterility in patient procedures. Materials that could be resterilized may be suitable depending upon the rigid guidelines defined by OSHA (Occupational Safety Hazards Administration), JCAHO (Joint Commision for the Accreditation of Hospitals Organization), and other governing agencies that relate to the standards of procedures hospitals, out-patient clinics and private physician's offices must adhere to.

The shield 12 is basically formed in a shape of an arc that fits around the hand 6. At the top and bottom apexes of the arc, provisions are made for attaching and securing the transducer 8. The provisions can be as simple as an opening with hook and loop material or as elaborate as specialty latches or clamps designed to specifically attach to a transducer 8.

The preferred embodiment and the best mode contemplated of the protection device for hand held ultrasound needle procedures of the present invention are herein described. However, it should be understood that the best mode for carrying out the invention hereinafter described is offered by way of illustration and not by the way of limitation. It is intended that the scope of the invention includes all modifications that incorporate its principal design features.

The protection device for hand held ultrasound needle procedures 10, in the preferred embodiment, consists of a shield 12 made from a needle resistant material. The shield 12 is bent into the shape basically described as an arc 14. The shield 12 can be made as a flexible shield 12, FIG. 1, or as a rigid shield, FIG. 2. A shield 12 made from a flexible material will be bent into a shape of an arc 14 at the time of use. If made from a rigid material, the shield 12 would be in a permanent shape of an arc. The only requirements for the material are that the material must be puncture resistant to needle punctures (by both hand directed and mechanically fired as in a biopsy gun), be readily cleaned, autoclavable or, in a preferred embodiment disposable to ensure sterility, sturdy enough to make the shield 12, and strong enough for attachment to and being secured to a transducer, and yet also be suitable for medical applications. Typical materials would include, but are not limited to, lightweight metals, polyresins, acrylics and flexible materials such as Kevlar.

Generally, if the shield 12 is made from a flexible material, the shield 12 can be easily stored in a flat position, shipped and transported in a flat envelope type container. See FIG. 1. The container will typically hold the shield 12 in a sterile environment.

Another embodiment, the shield 12 is made from a rigid material, such as plastic. See FIG. 2. The shield 12 is in a permanently held shape of an arc 14. A durable plastic lexan plexiglass was used as a prototype and served very well. The shield 12 could be either made in an arc during manufacture or later bent into an arc 14 by a manufacturing process. This embodiment is preferred by many because it is rigid and does not flex during use. The plastic embodiment can also be stored in a sterile container, but is generally more bulky than the envelope type container used with the flat embodiment.

The arc 14 has a first apex 16 and a second apex 18. The first apex 16 is located at an upper end of the arc 14. The second apex 18 is located at a lower end of the arc 14.

A first receiving means 20, for receiving an upper end of a transducer or other similar device, is positioned at the first apex 16. The first receiving means 20, in a preferred embodiment, can be described as an opening or open area to allow the upper end of the transducer, transducer cable, or other similar device to pass through or past the shield 12 at the apex 16. In another configuration, not shown, the first receiving means 20 is simply a clamp or latch attached to the apex 16. The clamp would have an opening or open area. The opening allows the top end of the transducer, or cable therefore, to pass through and would be considered the first receiving means.

Figure 2:
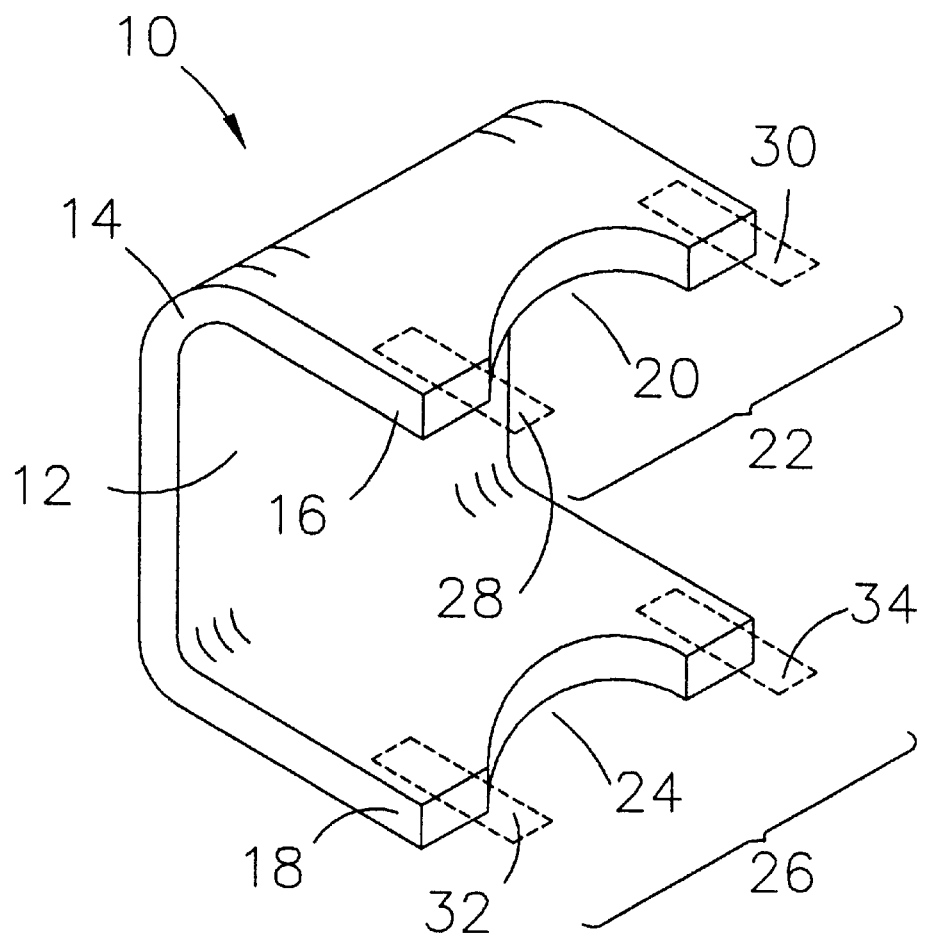
FIG. 2 shows the protective device of this invention with the shield made from a rigid material and bent into an arc, which is a representation of another embodiment.
Figure 3:
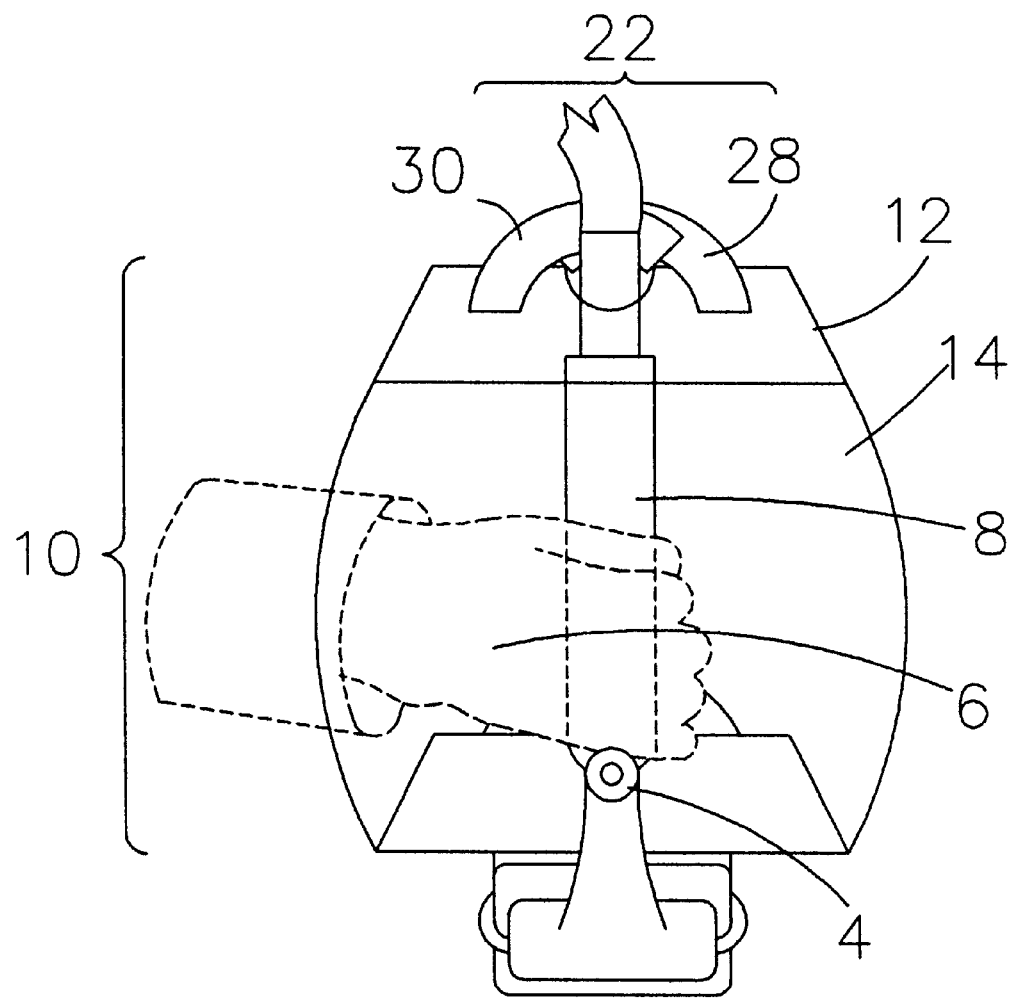
FIG. 3 showing a typical front view of the protection device for hand held ultrasound needle procedures attached to a transducer with a hand inside the shield holding the transducer.
Figure 4:
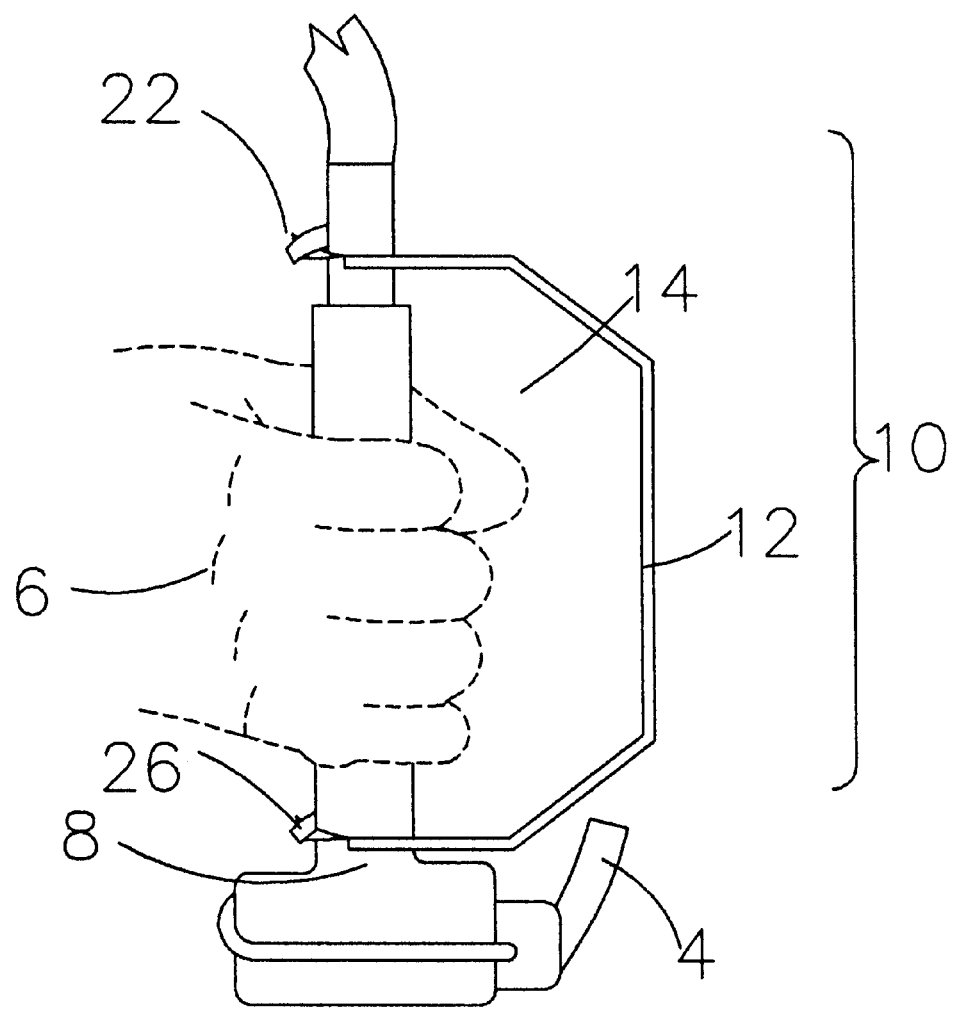
FIG. 4 shows a side view of the protection device for hand held ultrasound needle procedures attached to a transducer with a hand inside the shield holding the transducer.

A first securing means 22 is located at and attached to the first apex 16 for securing the transducer, transducer cable, or similar device in the first receiving means 20. In a simple configuration as shown in FIGS. 1 and 2, the first securing means 22 is hook and loop straps 28 and 30 attached on opposite or opposing sides of the first receiving means 20. As the transducer 8 is positioned in the first receiving means 20, the hook and loop straps 28 and 30 secures the transducer 8. If a clamp or latch is used as described above, the clamp would be closed and/or tightened to secure the transducer within the open area or first receiving means 20 of the clamp. This is pretty much self explanatory, and as such a drawing is not necessarily needed to understand this concept.

In a preferred embodiment, the first receiving means 20 is simply a notched out area of the first apex 16, as shown in FIGS. 1 and 2. The notched out area can be either rectangular, FIG. 1, or circular, FIG. 2, in shape. A simple hole through the apex 16 could also be used if the transducer or the connection at the end of the cable fits through the hole.

Other configurations that function equivalently to receive and secure a transducer should also be considered within the scope of this invention. The only requirement of the first receiving means and first securing means is that the cable or top of the transducer, or similar device be allowed to pass thereby or through and yet be secured to the shield.

A second receiving means 24, for receiving a lower end or head of a transducer or similar device, is positioned at the end of the second apex 18. The second receiving means 24 is such that a head of the transducer or similar device is allowed to be exposed and used without obstruction as intended and designed. A second securing means 26, for securing the lower end of a transducer, the transducer head, or similar device, is located on the second apex 18. These can be similar or different from the first receiving means 20 and first securing means 22.

Figure 1A:
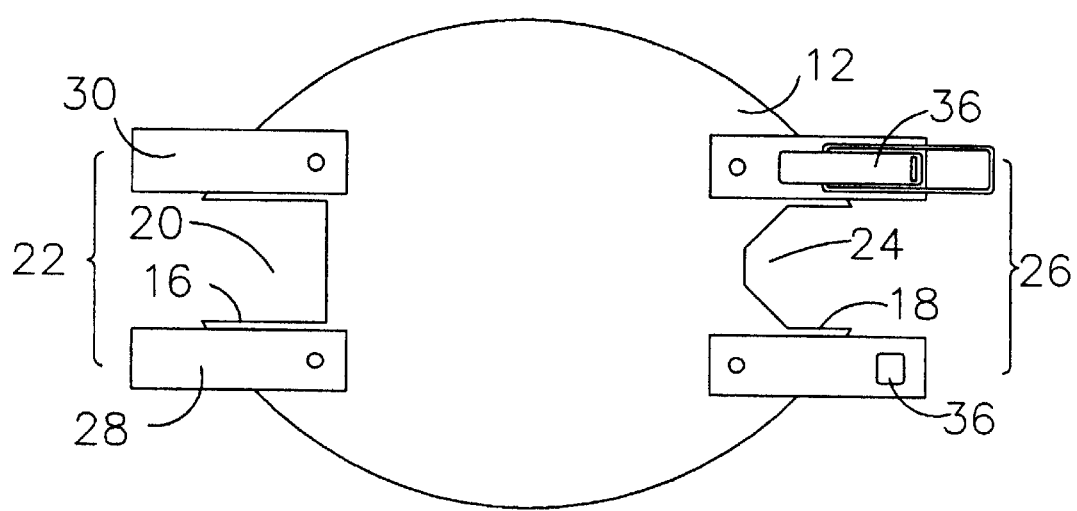
FIG. 1A shows the protective device as shown in FIG. 1 with one type of a latch that could be used as a securing means.

FIG. 1A shows one type of a typical latch 36 as a securing means 26 to secure a transducer or similar device within the receiving means 24.

In the preferred embodiment, the second receiving means 24 and second securing means 26 is similar to the first receiving means 20 and first securing means 22. That is, the second receiving means 24 would be an opening or notched out area for receiving the transducer 8. The transducer 8 is secured in the second receiving area 24 by the second securing means 26 by a pair of opposing hook and loop straps 32 and 34, in the preferred embodiment, or with a clamp or latch in other embodiments as previously descibed.

There are different shaped transducers as previously indicated. The preferred embodiment described above would be universally adaptable for virtually all types. However, there are also desires and applications for protective devices 10 for ultrasound procedures of this invention made specific to specific types of transducers. In these instances, the second receiving means 24 would be made specific to the transducer. The specific second receiving means 24 could be an opening or notched out area made to the specific shape of the head of the transducer, or a specific clamp or latch designed to interact with a specific transducer(s) be attached. By being specific, the shield 12 could be attached in an exact position. This would prevent the shield 12 from rotating about the transducer during use. Some manufactures may also prefer specific equipment to be used with their devices. This method satisfies that need.

The shield 12 of this invention, whatever the configuration, is secured on the transducer 8, or similar device. The operator's hand can grasp a handle area on the transducer 8, or similar device, between the apexes 16 and 18, of shield 12. The shield 12 when properly secured will enclose and protect the operator's hand from inadvertent needle punctures.

In operation, the transducers is positioned within the first and second receiving means 20 and 24 and then secured by the first securing means and second securing means 22 and 26. If the configuration is a flexible shield 12, the shield 12 would be bent into an arc 14 during attachment. The technologist or physician can then insert their hand 6 into the arc 14 of the shield 12 to grasp the transducer 8. The transducer 8 can then be used in the normal manner. As the physician performs a biopsy, aspiration, stent, catheter placement or any other procedure in which the attached needle guide 4 is used, the technologist's hand is protected from needle punctures.

In the preferred embodiment described above, the protective device 10 is attached to the transducer 8 by the adjustable hook and loop straps 28, 30, 32 and 34. This allows for a universal and customized fit for both the user and the particular transducer 8 or other device being used. The lower end 18 of the shield 12 attaches above or over the biopsy needle guide 4 or directly to the transducer 8 or transducer head depending upon the design and configuration. The upper end 16 of the shield 12 would attach to the upper handle area of the transducer or cable extending therefrom. This allows the technologist/physician to grasp the transducer in a normal manner while providing a strong barrier between the directed biopsy needle and the technologist's hand. Under normal conditions, the protective device 10, when properly used and attached as described herein has proven to be virtually impervious to penetration by needles.

Having described the invention in detail, those skilled in the art will appreciate that modifications may be made of the invention without departing from the spirit of the inventive concept herein described.

Therefore, it is not intended that the scope of the invention be limited to the specific and preferred embodiments illustrated and described. Rather, it is intended that the scope of the invention be determined by the appended claims and their equivalents.

What is claimed is:

1. A protection device for hand held ultrasound needle procedures comprising:

a shield made from a needle resistant material bendable into an arc, said arc having a first apex and a second apex, said first apex located at an upper end of said arc and said second apex located at a lower end of said arc;

a first receiving means comprising a shape, a notched out area, or a hole through said shield at said first apex for receiving an upper end of a transducer or other similar device, said first receiving means allowing said upper end of said transducer, transducer cable, or other similar device to pass thereby;

a first securing means at said first receiving means for securing said transducer, transducer cable, or similar device within said first receiving means;

a second receiving means comprising a shape, a notched out area, or a hole through said shield at said second apex for receiving a lower end of a transducer, or similar device, such that a head of said transducer or similar device is allowed to be used without obstruction; and a second securing means at said second receiving means for securing said lower end of a transducer or similar device in said second receiving means, thereby securing said shield on said transducer or similar device such that an operator's hand can grasp said transducer, or similar device, between said apexes of said shield so the operator's hand is enclosed within said shield.

2. The protection device for hand held ultrasound needle procedures as set forth in claim 1 in which said shield is made from plastic and permanently bent into an arc to form said shield.

3. The protection device for hand held ultrasound needle procedures as set forth in claim 1 in which said shield is made from a flexible needle resistant material which is bendable into an arc at the time of application and attachment to a transducer or similar device.

4. The protection device for hand held ultrasound needle procedures as set forth in claim 1 in which said shield is made from an autoclavable material.

5. The protection device for hand held ultrasound needle procedures as set forth in claim 1 in which first securing means comprises hook and loop straps attached to opposing sides of said first receiving means.

6. The protection device for hand held ultrasound needle procedures as set forth in claim 1 in which said second securing means comprises hook and loop straps attached to opposing sides of said second receiving means.

7. The protection device for hand held ultrasound needle procedures as set forth in claim 1 in which said first securing means comprises a clamp or latch attached to said first apex of said shield, whereby a transducer cable, cord or upper portion of a transducer can pass therethrough and be secured within said receiving means.

8. The protection device for hand held ultrasound needle procedures as set forth in claim 1 in which said second receiving means comprises a specific clamp or latch attached to said apex and having an opening or an open area designed to interact with a specific transducer or similar device and said clamp or latch designed to secure said device within said opening or open area.

9. The protection device for hand held ultrasound needle procedures as set forth in claim 1 in which said shield is made from a disposable material.

10. The protection device for hand held ultrasound needle procedures as set forth in claim 1 in which said shield is made from aluminum or other light weight metal.

11. The protection device for hand held ultrasound needle procedures comprising:
   a shield made from a needle resistant material bendable into an arc, said arc having a first apex and a second apex, said first apex located at an upper end of said arc and said second apex located at a lower end of said arc;
   a first receiving means at said first apex for receiving an upper end of a transducer or other similar device, said receiving means comprising an open area, a notched out area, or a specifically shaped area at said first apex, said first receiving means allowing said upper end of said transducer, transducer cable, or other similar device to pass thereby;
   a first securing means for securing said transducer, transducer cable, or similar device within said first receiving means, said first securing means comprising straps of hook and loop material attached to opposing sides of said first receiving means;
   a second receiving means at said second apex for receiving a lower end of a transducer, or similar device, said second receiving means comprising an open area, a notched out area or a specifically shaped area in said second apex such that a head of said transducer or similar device is allowed to be used without obstruction; and
   a second securing means for securing said lower end of a transducer or similar device in said second receiving means, said second securing means comprising straps of hook and loop material attached to opposing sides of said second receiving means, thereby securing said shield on said transducer or similar device such that an operator's hand can grasp said transducer, or similar device, between said apexes of said shield so the operator's hand is enclosed within said shield.

12. The protection device for hand held ultrasound needle procedures as set forth in claim 11 in which said shield is made from a rigid material and permanently bent into an arc to form said shield.

13. The protection device for hand held ultrasound needle procedures as set forth in claim 11 in which said shield is made from a flexible needle resistant material which is bendable into an arc at the time of application and attachment to a transducer or similar device.

14. A protection device for hand held ultrasound needle procedures comprising:
   a shield made from a needle resistant material bendable into an arc, said arc having a first apex and a second apex, said first apex located at an upper end of said arc and said second apex located at a lower end of said arc;
   a first receiving means at said first apex for receiving an upper end of a transducer or other similar device, said first receiving means allowing said upper end of said transducer, transducer cable, or other similar device to pass thereby;
   a first securing means at said first receiving means for securing said transducer, transducer cable, or similar device within said first receiving means;
   a second receiving means at said second apex, said second receiving means comprises a specific shaped notched out area designed to receive a lower end of a specific transducer or similar device, such that a head of said transducer or similar device is allowed to be used without obstruction; and
   a second securing means at said second receiving means for securing said lower end of a transducer or similar device in said second receiving means, thereby securing said shield on said transducer or similar device such that an operator's hand can grasp said transducer, or similar device, between said apexes of said shield so the operator's hand is enclosed within said shield.

15. The protection device for hand held ultrasound needle procedures comprising:
   a shield made from a needle resistant material bendable into an arc, said arc having a first apex and a second apex, said first apex located at an upper end of said arc and said second apex located at a lower end of said arc;
   a first receiving means at said first apex for receiving an upper end of a transducer or other similar device, said receiving means comprising an open area at said first apex, said first receiving means allowing said upper end of said transducer, transducer cable, or other similar device to pass thereby;
   a first securing means for securing said transducer, transducer cable, or similar device within said first receiving means, said first securing means comprising straps of hook and loop material attached to opposing sides of said first receiving means;
   a second receiving means at said second apex for receiving a lower end of a transducer, or similar device, said second receiving means comprising a specific shaped open area or notched out area designed to receive a specific transducer or similar device such that a head of said transducer or similar device is allowed to be used without obstruction; and
   a second securing means for securing said lower end of a transducer or similar device in said second receiving means, said second securing means comprising straps of hook and loop material attached to opposing sides of said second receiving means, thereby securing said shield on said transducer or similar device such that an operator's hand can grasp said transducer, or similar device, between said apexes of said shield so the operator's hand is enclosed within said shield.

\* \* \* \* \*